(12) United States Patent
Duval et al.

(10) Patent No.: US 9,902,685 B2
(45) Date of Patent: Feb. 27, 2018

(54) USE OF NITROOXY ORGANIC MOLECULES IN FEED FOR REDUCING METHANE EMISSION IN RUMINANTS, AND/OR TO IMPROVE RUMINANT PERFORMANCE

(71) Applicant: DSM IP ASSETS B.V., Heerlen (NL)

(72) Inventors: Stephane Duval, Carspach (FR); Maik Kindermann, Liestal (CH)

(73) Assignee: DSM IP ASSETS B.V., Heerlen (NL)

(*) Notice: Subject to any disclaimer, the term of this patent is extended or adjusted under 35 U.S.C. 154(b) by 196 days.

(21) Appl. No.: 14/848,269

(22) Filed: Sep. 8, 2015

(65) Prior Publication Data
US 2015/0376113 A1 Dec. 31, 2015

Related U.S. Application Data

(62) Division of application No. 13/996,026, filed as application No. PCT/EP2011/072707 on Dec. 20, 2011.

(30) Foreign Application Priority Data

Dec. 20, 2010 (EP) .................................... 10195857
Aug. 26, 2011 (EP) .................................... 11178994

(51) Int. Cl.
| | | |
|---|---|---|
| A61K 31/455 | (2006.01) | |
| C07C 203/04 | (2006.01) | |
| A61K 31/21 | (2006.01) | |
| A61K 31/216 | (2006.01) | |
| A61K 31/22 | (2006.01) | |
| A61K 31/34 | (2006.01) | |
| A61K 31/345 | (2006.01) | |
| A61K 31/4406 | (2006.01) | |
| A61K 45/06 | (2006.01) | |
| C07C 311/03 | (2006.01) | |
| C07D 213/82 | (2006.01) | |
| C07D 307/72 | (2006.01) | |
| C07D 493/04 | (2006.01) | |
| A61K 31/04 | (2006.01) | |
| A61K 31/045 | (2006.01) | |
| A61K 31/08 | (2006.01) | |
| A61K 31/18 | (2006.01) | |
| A61K 31/24 | (2006.01) | |
| A61K 31/275 | (2006.01) | |
| C07C 207/02 | (2006.01) | |
| C07C 207/04 | (2006.01) | |
| C07C 255/11 | (2006.01) | |
| C07C 311/24 | (2006.01) | |
| A23K 20/105 | (2016.01) | |
| A23K 20/10 | (2016.01) | |
| A23K 50/10 | (2016.01) | |
| A23K 20/111 | (2016.01) | |
| A23K 20/121 | (2016.01) | |

(52) U.S. Cl.
CPC ............ *C07C 203/04* (2013.01); *A23K 20/10* (2016.05); *A23K 20/105* (2016.05); *A23K 20/111* (2016.05); *A23K 20/121* (2016.05); *A23K 50/10* (2016.05); *A61K 31/04* (2013.01); *A61K 31/045* (2013.01); *A61K 31/08* (2013.01); *A61K 31/18* (2013.01); *A61K 31/21* (2013.01); *A61K 31/216* (2013.01); *A61K 31/22* (2013.01); *A61K 31/24* (2013.01); *A61K 31/275* (2013.01); *A61K 31/34* (2013.01); *A61K 31/345* (2013.01); *A61K 31/4406* (2013.01); *A61K 45/06* (2013.01); *C07C 207/02* (2013.01); *C07C 207/04* (2013.01); *C07C 255/11* (2013.01); *C07C 311/03* (2013.01); *C07C 311/24* (2013.01); *C07D 213/82* (2013.01); *C07D 307/72* (2013.01); *C07D 493/04* (2013.01); *Y02P 60/56* (2015.11)

(58) Field of Classification Search
None
See application file for complete search history.

(56) References Cited

U.S. PATENT DOCUMENTS

| | | |
|---|---|---|
| 2003/0013198 A1 | 1/2003 | Harada |
| 2005/0137191 A1 | 6/2005 | Thatcher et al. |

(Continued)

FOREIGN PATENT DOCUMENTS

| | | |
|---|---|---|
| EP | 0 685 169 | 12/1995 |
| EP | 2 713 766 | 6/2015 |

(Continued)

OTHER PUBLICATIONS

Ungerfeld et al., Journal of Applied Microbiology 2004, 97, 520-526.*

(Continued)

*Primary Examiner* — Sreeni Padmanabhan
*Assistant Examiner* — Jeanmarie Calvillo
(74) *Attorney, Agent, or Firm* — Nixon & Vanderhye P.C.

(57) ABSTRACT

The present invention relates to a method for reducing the production of methane emanating from the digestive activities of a ruminant and/or for improving ruminant animal performance by using, as active compound at least one organic molecule substituted at any position with at least one nitrooxy group, or a salt thereof, which is administrated to the animal together with the feed. The invention also relates to the use of these compounds in feed and feed additives such as premix, concentrates and total mixed ration (TMR) or in the form of a bolus.

5 Claims, No Drawings

(56) References Cited

U.S. PATENT DOCUMENTS

| | | |
|---|---|---|
| 2007/0098796 A1 | 5/2007 | Rekhi et al. |
| 2008/0207713 A1 | 8/2008 | Wang et al. |
| 2010/0179192 A1 | 7/2010 | Impagnatiello et al. |
| 2014/0147529 A1* | 5/2014 | Duval .................. A23K 1/1646 424/754 |

FOREIGN PATENT DOCUMENTS

| | | |
|---|---|---|
| GB | 1 268 952 | 3/1972 |
| WO | 86/06960 | 12/1986 |
| WO | 01/26482 | 4/2001 |
| WO | 2007/053392 | 5/2007 |
| WO | 2010/072584 | 7/2010 |
| WO | 2011/010921 | 1/2011 |
| WO | 2012/160191 | 11/2012 |

OTHER PUBLICATIONS

International Search Report for PCT/EP2011/072707, dated Jun. 11, 2012.

Fagerholm et al., "Pre-clinical pharmacokinetics of the cyclooxygenase-inhibiting nitric oxide donor (CINOD) AZD3582", *Journal of Pharmacy and Pharmacology*, vol. 57, No. 5, May 1, 2005, pp. 587-598.

Anderson et al., "Effects of select nitrocompounds on in vitro ruminal fermentation during conditions of limiting or excess added reductant", *Bioresource Technology*, vol. 99, No. 18, Dec. 1, 2008, pp. 8655-8661.

Busquet et al., "Effect of garlic oil and four of its compounds on rumen microbial fermentation", *Journal of Dairy Science, American Dairy Science Association*, vol. 88, Jan. 1, 2005, pp. 4393-4404.

Morgavi, et al, Animal (2010), 4:7, pp. 1024-1036 & The Animal Consortium 2010 (Apr. 13, 2010).

Anderson, R.A. et al, Journal of Andrology, vol. 30, No. 2, Mar./Apr. 2009.

Balderston, W.L., Applied and Environmental Microbiology, Aug. 1976, p. 264-269.

Li, D.H. et al, Rev Columb Cienc Peuc 2010; 23:44-450.

NZ Office Action dated May 29, 2014.

NZ Office Action dated Jun. 30, 2014.

Amyl nitrate, https://web.archive.org/web/20100601075134/http://en.wikipedia.org/wiki/Amyl_nitrate.

J. Haisan et al; "The effects of feeding 3-nitrooxypropanol on methane emissions and productivity of Holstein cows in mid lactation", J. Dairy Sci. 97:3110-3119 (2014).

Bozic, et al, Bioresource Technology 100 (2009) 4017-4025.

Reynolds, et al, Journal of Dairy Science, vol. 97, Issue 6, Jun. 2014, pp. 3777-3789.

Martinez-Fernandez, Journal of Dairy Science, vol. 97, Issue 6, Jun. 2014, pp. 3790-3799.

Haisan, et al, Journal of Dairy Science, vol. 97, Issue 5, May 2014, pp. 3110-3119.

CN Office Action dated Jan. 14, 2015 in Chinese Application No. 201180061610.7.

Institute of Dairy Science, Chinese Journal of Animal Nutrition, 2012,22(2):386-392.

Tugtas et al, Biotechnology and Bioengineering, vol. 96, No. 3, Feb. 15, 2007_2006 Wiley Periodicals, Inc. p. 444.

* cited by examiner

USE OF NITROOXY ORGANIC MOLECULES IN FEED FOR REDUCING METHANE EMISSION IN RUMINANTS, AND/OR TO IMPROVE RUMINANT PERFORMANCE

This application is a divisional of commonly owned U.S. application Ser. No. 13/996,026, filed Sep. 23, 2013 (now U.S. Pat. No. 9,266,814), which is the national phase application under 35 USC §371 of PCT/EP2011/072707, filed Dec. 20, 2011 which designated the US and claims benefit of European Application No. 10195857.7, filed Dec. 20, 2010 and European Application No. 11178994.7, filed Aug. 26, 2011, the entire contents of each of which are hereby incorporated by reference.

The present invention relates to the use of at least one organic molecule substituted at any position with at least one nitrooxy group for reducing the production of methane emanating from the digestive activities of ruminants, and/or to improve the ruminant performance.

The present invention also relates to animal feed or animal feed compositions and feed additives comprising the above mentioned molecules. The term feed or feed composition means any compound, preparation, mixture, or composition suitable for, or intended for intake by an animal.

In the present context, a ruminant is a mammal of the order Artiodactyla that digests plant-based food by initially softening it within the animal's first stomach, known as the rumen, then regurgitating the semi-digested mass, now known as cud, and chewing it again. The process of again chewing the cud to further break down plant matter and stimulate digestion is called "ruminating".

Rumen fermentation brings some disadvantages. Methane is produced as a natural consequence of the anaerobic fermentation, which represents an energy loss to the host animal. Carbohydrate makes up 70-80% of the dry matter in a typical dairy cattle ration and in spite of this the absorption of carbohydrates from the gastro-intestinal tract is normally very limited. The reason for this is the extensive fermentation of carbohydrates in the rumen resulting in production of acetate, propionate and butyrate as the main products. These products are part of the so called volatile fatty acids, (VFAs).

Besides the energy loss, methane is also a greenhouse gas, which is many times more potent than $CO_2$. Its concentration in the atmosphere has doubled over the last century and continues to increase alarmingly. Ruminants are the major contributors to the biogenic methane formation, and it has been estimated that the prevention of methane formation from ruminants would almost stabilize atmospheric methane concentrations.

Furthermore, the assessment of the Kyoto protocol followed by the Copenhagen climate summit in 2009 places increased priority in decreasing methane emissions as part of a multi-gas strategy. The most effective additives currently used for reducing the formation of methane contain antibiotics which diminish the proliferation of microorganisms providing hydrogen ($H_2$) to the methanogens (Sauer et al. 1998. American Society of Animal Science; 76: 906-914). However, the effect of antibiotics on the formation of methane has some disadvantages because of rapid adaptation of the microflora and/or resistance development leading to a complete loss of the intended effect within a short period of time (2 to 3 weeks), and because the use of antibiotics is banned in Europe for non therapeutic use.

Non antibiotic products (bile acid derivatives) leading to reduction of methane emission, when tested using an in vitro rumen simulation model, have recently been published (WO 2010072584). However, the amount required to produce a moderate reduction of methane emission are not compatible with the ruminant feed industry cost constraints.

Furthermore, a number of natural plant extracts (Garlic: WO 2009150264, yucca, cinnamon, rhubarb . . . ) have been described in the scientific literature as potent solutions to reduce methane emission in ruminants based on in vitro experiments. However, none of these solutions made it to a commercial product because of side effects (residues in milk), because of lack efficacy, when tested in vivo, or because of the very large amount of additive which needs to be supplied to the animal to generate a significant methane reduction.

Under these circumstances there is still a need to develop new substances which reduce the formation of methane and which are in line with reliable and generally accepted practice and not of a medicinal nature. In addition to reducing methane emission, such substances may also contribute to improve ruminant performance by improving the feed conversion ratio, reducing feed intake, improving weight gain, and/or improving carcass, or milk yield.

The present inventors now surprisingly found that the compounds specified herein after, have a great potential for use in animal feed in order to essentially reduce the formation of methane without affecting microbial fermentation in a way that would be detrimental to the host animal. Moreover, the compounds of the present invention also have a great benefit regarding overall animal performance as measured by feed conversion ratio, feed intake, weight gain, carcass yield, or milk yield. Said compounds are also more stable than those described in the prior art, safer for the animal and human, lead to persistent methane reduction effect, they do not affect palatability, they can be produced at industrial scale at a cost compatible with the animal nutrition industry, and above all, they do not provoke accumulation of any metabolite in the milk or meat of the supplemented animal, and they are active at very low concentration in the rumen.

In particular, the present inventors have observed that the feeding to ruminants of at least one organic molecule substituted at any position with at least one nitrooxy group is very effective for reducing the production of methane emanating from the digestive activities of ruminants without negatively affecting total VFA production, and/or for improving the ruminant performance. Moreover, the present inventors have shown that when the nitrooxy group is replaced by other chemical groups of similar physicochemical properties, the technical effect on methane production is lost demonstrating that the Nitrooxy group is key for the effect on methane reduction of the present invention.

It is known from the international patent application Nr.: PCT/EP2010/069338 that nitrooxy-carboxylic acid derivatives are potent inhibitors of rumen methanogenesis in vitro, and also in vivo. Therefore, these molecules are specifically disclaimed from the present invention.

Therefore, the present invention provides the use of at least one organic molecule substituted at any position with at least one nitrooxy group, or a salt thereof as defined by formula (I) as an active compound in animal feeding for reducing the formation of methane emanating from the digestive activities of ruminants and/or for improving ruminant performance.

The invention further provides a method for reducing the production of methane emanating from the digestive activities of ruminants and/or for improving ruminant animal performance, comprising orally administering a sufficient amount of at least one organic molecule substituted at any position with at least one nitrooxy group, or a salt thereof as defined by formula (I) to the animal. It is to be understood by oral administration a simple feeding, or manual administration of a bolus.

In all embodiments of the present invention, organic molecules substituted at any position with at least one nitrooxy group, or salts thereof are defined by the following compound of formula (I)

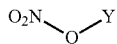

formula (I)

wherein Y is an organic molecule of the following composition: $C_aH_bO_dN_eS_g$, wherein a is comprised between 1 and 25, preferably between 1 and 10 b is comprised between 2 and 51, preferably between 2 and 21 d is comprised between 0 and 8, preferably between 0 and 6 e is comprised between 0 and 5, preferably between 0 and 3 g is comprised between 0 and 3, preferably between 0 and 1, wherein nitrooxy alkanoic acid, and/or derivatives thereof as defined by the formula (II) are excluded,

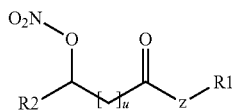

formula (II)

wherein u is comprised between 0 and 23 and, wherein if u≠0, the carbon chain is a linear, a cyclic, or branched linear or cyclic aliphatic carbon chain which may be mono- or polyunsaturated and in any isomeric form, Z is independently O, NH, or N—R3, wherein if R1≠H, Z—R1 represents an ester or a secondary amide derivative, R1 is independently, hydrogen or a saturated straight, cyclic or branched chain of an alkyl or alkenyl group containing 1 to 10 carbon atoms, R2 is independently, hydrogen or a saturated straight or branched chain of an alkyl or alkenyl group containing 1 to 23 carbon atoms, and R3 is independently, hydrogen or a saturated straight, cyclic or branched chain of an alkyl or alkenyl group containing 1 to 10 carbon atoms.

In another embodiment, preferred compounds of formula (I) according to the present invention are compounds, wherein a is comprised between 1 and 10, preferably, a is comprised between 3 and 8.

In another embodiment, preferred compounds of formula (I) according to the present invention are compounds of formula (III),

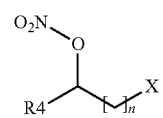

formula (III)

wherein n is comprised between 0 and 12, preferably comprised between 0 and 6 and, wherein, if n≠0, the carbon chain is a linear, a cyclic, or branched aliphatic carbon chain which may be non substituted or substituted with up to 3 hydroxyl-, alkoxy-, amino-, alkylamino-, dialkylamino- or nitrooxy groups, or an alkenyl, or an alkynyl carbon chain mono- or polyunsaturated and in any isomeric form, R4 is independently, hydrogen or a saturated straight, cyclic or branched chain of an alkyl or alkenyl group containing 1 to 12, preferably 1 to 6 carbon atoms, X is hydrogen, R5, R5≡N, —OR5, —OCOR5, —NR5R6, —ONO2, —COOR5, —CONR5R6, —NHSO2R5, or —SO2NHR5, R5 and R6 are independently, hydrogen, C1-C12 straight, branched or cyclic alkyl chain, non substituted or substituted with up to 3 hydroxyl-, alkoxy-, amino-, alkylamino-, dialkylamino- or nitrooxy groups, alkenyl, or alkynyl carbon chain which may be mono or polyunsaturated, and in any isomeric form.

For all embodiments of the present invention, it is to be understood that compounds of formula (I) and compounds of formula (III) can be in any isomeric form.

It is to be understood in the above definition of compounds of formula (III) that when n>2, the carbon chain can be linear or branched at any position along the carbon chain. In addition, the carbon chain can be branched by multiple branches at different positions along the carbon chain. Moreover, when n>3, the aliphatic carbon chain may form a cyclic moiety. This cyclic moiety can carry the nitrooxy moiety at any position (2, 3, 4), and it can also be branched at multiple positions by any aliphatic groups. The branched aliphatic groups are preferably, methyl, ethyl or propyl. Moreover, the carbon chain may be further substituted with up to 3 hydroxyl-, alkoxy-, amino-, alkylamino-, dialkylamino- or nitrooxy groups.

In the above definition of derivatives of the formula (III) a preferred alkyl group is methyl, ethyl, propyl, isopropyl, butyl, sec. butyl, isobutyl, pentyl, neopentyl, hexyl, cyclohexyl, and 2-ethyl-hexyl and octyl. Furthermore any alkyl or alkenyl group containing three or more carbon atoms can be straight chain, branched, or cyclic. In addition for the straight chain or branched $C_2$-$C_{10}$-alkenylene group, this is understood to encompass alkenylene groups with one or (from $C_4$) more double bonds; examples of such alkenylene groups are those of the formulae —CH═CH—, —CH═CH—CH$_2$—, —CH═CH—(CH$_2$)$_3$— and —(CH═CH)$_2$—.

In another embodiment, more preferred compounds of formula (I) according to the present invention are selected from the list of compounds, and salts thereof comprising: 3-Nitrooxypropanol, racemate-4-Phenylbutane-1,2-diyl dinitrate, 2-(Hydroxymethyl)-2-(nitrooxymethyl)-1,3-propanediol, N-Ethyl-3-nitrooxy-propionic sulfonyl amide, 5-Nitrooxy-pentanenitrile, 5-Nitrooxy-pentane, 3-Nitrooxy-propyl propionate, 1,3-bis-Nitrooxypropane, 1,4-bis-Nitrooxybutane, 1,5-bis-Nitrooxypentane, 3-Nitrooxy-propyl benzoate, 3-Nitrooxy-propyl hexanoate, 3-Nitrooxy-propyl 5-nitrooxy-hexanoate, Benzylnitrate, isosorbid-dinitrate, and N-[2-(Nitrooxy)ethyl]-3-pyridinecarboxamide, 2-Nitro-5-n itrooxymethyl-furan, and Bis-(2-nitrooxyethyl) ether as listed in Table 1:

TABLE 1

Preferred compounds of formula (I) according to the present invention

| Comp. Identifier | Molecular structure | Chemical name |
|---|---|---|
| 1 | HO-CH₂CH₂CH₂-O-NO₂ | 3-Nitrooxypropanol |
| 2 | Ph-CH₂CH₂-CH(ONO₂)-CH₂-ONO₂ | rac-4-Phenylbutane-1,2-diyl dinitrate |
| 3 | C(CH₂OH)₃(CH₂ONO₂) | 2-(Hydroxymethyl)-2-(nitrooxymethyl)-1,3-propanediol |
| 4 | EtNH-SO₂-CH₂CH₂CH₂-O-NO₂ | N-Ethyl-3-nitrooxy-propionic sulfonyl amide |
| 5 | O₂N-O-CH₂CH₂CH₂CH₂-C≡N | 5-Nitrooxy-pentanenitrile |
| 6 | O₂N-O-CH₂CH₂CH₂CH₂CH₃ | 5-Nitrooxy-pentane |
| 7 | CH₃CH₂-C(O)-O-CH₂CH₂CH₂-O-NO₂ | 3-Nitrooxy-propyl propionate |
| 8 | O₂N-O-CH₂CH₂CH₂-O-NO₂ | 1,3-bis-Nitrooxypropane |
| 9 | O₂N-O-CH₂CH₂CH₂CH₂-O-NO₂ | 1,4-bis-Nitrooxybutane |
| 10 | O₂N-O-CH₂CH₂CH₂CH₂CH₂-O-NO₂ | 1,5-bis-Nitrooxypentane |
| 11 | Ph-C(O)-O-CH₂CH₂CH₂-O-NO₂ | 3-Nitrooxy-propyl benzoate |
| 12 | CH₃(CH₂)₄-C(O)-O-CH₂CH₂CH₂-O-NO₂ | 3-Nitrooxy-propyl hexanoate |
| 13 | O₂N-O-CH₂CH₂CH₂CH₂-C(O)-O-CH₂CH₂CH₂-O-NO₂ | 3-Nitrooxy-propyl 5-nitrooxy-hexanoate |
| 14 | Ph-CH₂-O-NO₂ | Benzylnitrate |
| 15 | isosorbide dinitrate structure | isosorbid-dinitrate |

TABLE 1-continued

Preferred compounds of formula (I) according to the present invention

| Comp. Identifier | Molecular structure | Chemical name |
|---|---|---|
| 16 | 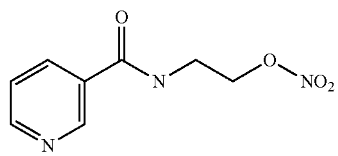 [SMILES: O=C(NCCO[N+](=O)[O-])c1cccnc1] | N-[2-(Nitrooxy)ethyl]-3-pyridinecarboxamide |
| 17 | 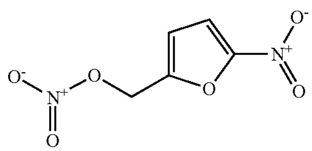 [SMILES: O=[N+]([O-])OCc1ccc([N+](=O)[O-])o1] | 2-Nitro-5-nitrooxymethyl-furan |
| 18 | 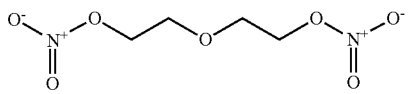 [SMILES: O=[N+]([O-])OCCOCCO[N+](=O)[O-]] | Bis-(2-nitrooxyethyl) ether |

In another embodiment, even more preferred compounds of formula (III) based on the strength of their effect in reducing methane are selected from the list of compounds, and salts thereof comprising: 3-Nitrooxypropanol, 5-Nitrooxy-pentanenitrile, 5-Nitrooxy-pentane, 3-Nitrooxy-propyl propionate, 1,3-bis-Nitrooxypropane, 1,4-bis-Nitrooxybutane, 1,5-bis-Nitrooxypentane, 3-Nitrooxy-propyl benzoate, 3-Nitrooxy-propyl hexanoate, 3-Nitrooxy-propyl 5-nitrooxy-hexanoate, isosorbid-dinitrate, and N-[2-(Nitrooxy)ethyl]-3-pyridinecarboxamide, and Bis-(2-nitrooxyethyl) ether as listed in Table 2:

TABLE 2

Most preferred compounds of formula (I) according to the present invention

| Comp. Identifier | Molecular structure | Chemical name |
|---|---|---|
| 1 | 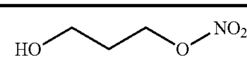 | 3-Nitrooxypropanol |
| 5 | 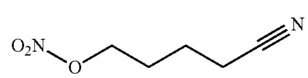 | 5-Nitrooxy-pentanenitrile |
| 6 | 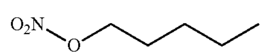 | 5-Nitrooxy-pentane |
| 7 | 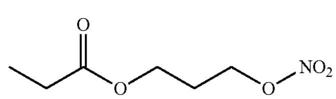 | 3-Nitrooxy-propyl propionate |
| 8 | 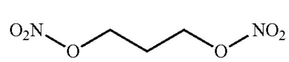 [SMILES: O=[N+]([O-])OCCCO[N+](=O)[O-]] | 1,3-bis-Nitrooxypropane |
| 9 | 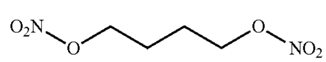 [SMILES: O=[N+]([O-])OCCCCO[N+](=O)[O-]] | 1,4-bis-Nitrooxybutane |
| 10 | 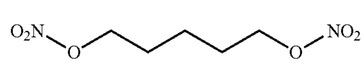 [SMILES: O=[N+]([O-])OCCCCCO[N+](=O)[O-]] | 1,5-bis-Nitrooxypentane |
| 11 | 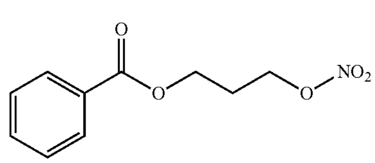 [SMILES: O=C(OCCCO[N+](=O)[O-])c1ccccc1] | 3-Nitrooxy-propyl benzoate |
| 12 | 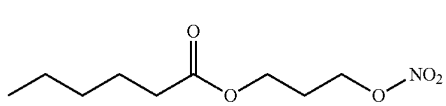 | 3-Nitrooxy-propyl hexanoate |

TABLE 2-continued

Most preferred compounds of formula (I) according to the present invention

| Comp. Identifier | Molecular structure | Chemical name |
|---|---|---|
| 13 | O₂N–O–(CH₂)₃–C(=O)–O–(CH₂)₃–O–NO₂ | 3-Nitr-oxy-propyl 5-nitrooxy-hexanoate |
| 15 | (isosorbide dinitrate structure) | Isosorbid-dinitrate |
| 16 | (pyridine-3-carboxamide with N-CH₂CH₂-O-NO₂) | N-[2-(Nitrooxy)ethyl]-3-pyridinecarboxamide |
| 18 | ⁻O–N⁺(=O)–O–CH₂CH₂–O–CH₂CH₂–O–N⁺(=O)–O⁻ | Bis-(2-nitrooxyethyl) ether |

In another embodiment, most preferred compound of formula (I) based on the strength of their effect in reducing methane and on the production process is a mixture of 3-nitrooxy propanol and 1,3-bis-nitrooxypropane. Preferably the ratio 3-nitrooxy propanol/1,3-bis-nitrooxypropane is comprised between 1/10 and 1000/1, more preferably, between 1/5 and 100/1, most preferably, between 1/1 and 10/1.

The compounds of the present invention also comprise salts of the nitrooxy organic molecule. Preferred cations for salt preparation may be selected from the group consisting of sodium (Na+), potassium (K+), lithium (Li+), magnesium (Mg2+), calcium (Ca2+), barium (Ba2+), strontium (Sr2+), and ammonium (NH4+). Salts may also be prepared from an alkali metal or an alkaline earth metal.

The compounds of the present invention can be manufactured in principle according to synthetic methods known per se for nitrooxy organic molecules, and/or based on methods as described in the examples.

In all these cases appropriate methods to purify the product (compounds of formula (I)) can be chosen by those skilled in the art, i.e. by column chromatography, or the compound of formula (I), can be isolated and purified by methods known per se, e.g. by adding a solvent such as diethyl-ether or ethyl acetate to induce the separation of the crude product from the mixture after reaction, and drying over Na₂SO₄ of the collected crude product.

Methane emission by ruminants can easily be measured in individual animals in metabolic chambers by methods known in the art (Grainger et al., 2007 J. Dairy Science; 90: 2755-2766). Moreover, it can also be assessed at barn level by an emerging technology using laser beam (McGinn et al., 2009, Journal of Environmental Quality; 38: 1796-1802). Alternatively, methane produced by a dairy ruminant can also be assessed by measurement of VFA profiles in milk according to WO 2009/156453.

Ruminant performance can be assessed by methods well known in the art, and is usually characterized by feed conversion ratio, feed intake, weight gain, carcass yield, or milk yield.

The present invention also relates to the use of at least one organic molecule substituted at any position with at least one nitrooxy group, or a salt thereof as defined by formula (I) in combination with at least one additional active substance which shows similar effects with regard to methane formation in the rumen and which is selected from the group consisting of diallyl disulfide, garlic oil, allyl isothiocyanate, deoxycholic acid, chenodeoxycholic acid and derivatives thereof.

Further components that could be given together with the compound according to the present invention are for example yeasts, essential oils, and ionophores like Monensin, Rumensin.

It is at present contemplated that diallyl disulfide, garlic oil, allyl isothiocyanate deoxycholic acid, chenodeoxycholic acid and derivatives thereof are independently administered in dosage ranges of for example 0.01-500 mg active substance per kg feed (ppm). These compounds are either commercially available or can easily be prepared by a skilled person using processes and methods well-known in the prior art.

Ruminating mammals according to the present invention include cattle, goats, sheep, giraffes, American Bison, European bison, yaks, water buffalo, deer, camels, alpacas, llamas, wildebeest, antelope, pronghorn, and nilgai.

For all embodiments of the present invention, domestic cattle, sheep and goat are the more preferred species. For the present purposes most preferred species are domestic cattle. The term includes all races of domestic cattle, and all production kinds of cattle, in particular dairy cows and beef cattle.

The present invention also relates to the use of at least one organic molecule substituted at any position with at least one nitrooxy group, or a salt thereof as defined by formula (I), wherein the methane production in ruminants calculated in liters per kilogram of dry matter intake is reduced by at least 10% when measured in metabolic chambers. Preferably, methane reduction is at least 15%, more preferably, at least 20%, even more preferably, at least 25%, most preferably, at least 30%. Alternative methane emission measurements may also be used like using a laser beam or for dairy ruminants, correlating methane production to the VFA profile in milk.

The present invention also relates to the use of at least one organic molecule substituted at any position with at least one nitrooxy group, or a salt thereof as defined by formula (I), wherein the ruminant feed conversion ratio is reduced by at least 1% when measured in conventional performance trial. Preferably, the feed conversion ratio is reduced by at least 2%, more preferably, by at least 2.5%, even more preferably, by at least 3%, most preferably, by at least 3.5%.

The present invention also relates to the use of at least one organic molecule substituted at any position with at least one nitrooxy group, or a salt thereof as defined by formula (I), wherein the amount of the at least one active compound as defined in formula (I) administered to the ruminant animal is from 1 mg to 10 g per Kg of feed, preferably from 10 mg to 1 g per Kg of feed, more preferably, from 50 mg to 500 mg per Kg of feed. For the use in animal feed, however, organic molecules substituted at any position with at least one nitrooxy group, or their salts thereof as defined by formula (I) need not be that pure; it may e.g. include other compounds and derivatives.

As indicated above, the compounds of the present invention are useful as compounds for feed additives and animal feed compositions for ruminants, and accordingly are useful as the active ingredients in such feed to reduce methane formation in the digestive tract of the animal, and/or to improve ruminant performance.

For the realisation of their use as such ingredients for the feed of ruminants the compounds may be incorporated in the feed by methods known per se in the art of feed formulation and processing.

Further aspects of the present invention are therefore formulations, i.e. feed additives and animal feed compositions containing compounds as herein above defined.

The present invention therefore also relates to a feed composition or a feed additive comprising at least one compound of formula (I) or a salt thereof. Preferably, the feed composition or feed additive is a ruminant base mix. In a preferred embodiment, the composition is a mineral premix, a vitamin premix including vitamins and minerals or a bolus.

The normal daily dosage of a compound according to the invention provided to an animal by feed intake depends upon the kind of animal and its condition. Normally this dosage should be in the range of from about 1 mg to about 10 g, preferably from about 10 mg to about 1 g, more preferably, 50 mg to 500 mg compound per kg of feed.

The at least one organic molecule substituted at any position with at least one nitrooxy group, or a salt thereof as defined by formula (I) may be used in combination with conventional ingredients present in an animal feed composition (diet) such as calcium carbonates, electrolytes such as ammonium chloride, proteins such as soya bean meal, wheat, starch, sunflower meal, corn, meat and bone meal, amino acids, animal fat, vitamins and trace minerals.

Particular examples of compositions of the invention are the following:
An animal feed additive comprising (a) at least one compound selected from table 1 and (b) at least one fat-soluble vitamin, (c) at least one water-soluble vitamin, (d) at least one trace mineral, and/or (e) at least one macro mineral;
An animal feed composition comprising at least one compound selected from table 1 and a crude protein content of 50 to 800 g/kg feed.

Therefore, in a preferred embodiment, the present invention relates to a ruminant feed composition or feed additive The so-called premixes are examples of animal feed additives of the invention. A premix designates a preferably uniform mixture of one or more micro-ingredients with diluents and/or carrier. Premixes are used to facilitate uniform dispersion of micro-ingredients in a larger mix.

Apart from the active ingredients of the invention, the premix of the invention contains at least one fat-soluble vitamin, and/or at least one water soluble vitamin, and/or at least one trace mineral, and/or at least one macro mineral. In other words, the premix of the invention comprises the at least one compound according to the invention together with at least one additional component selected from the group consisting of fat-soluble vitamins, water-soluble vitamins, trace minerals, and macro minerals.

Macro minerals may be separately added to the feed. Therefore, in a particular embodiment, the premix comprises the active ingredients of the invention together with at least one additional component selected from the group consisting of fat-soluble vitamins, water-soluble vitamins, and trace-minerals.

The following are non-exclusive lists of examples of these components:
Examples of fat-soluble vitamins are vitamin A, vitamin D3, vitamin E, and vitamin K, e.g. vitamin K3.
Examples of water-soluble vitamins are vitamin B12, biotin and choline, vitamin B1, vitamin B2, vitamin B6, niacin, folic acid and panthothenate, e.g. Ca—D-panthothenate.
Examples of trace minerals are manganese, zinc, iron, copper, iodine, selenium, and cobalt.
Examples of macro minerals are calcium, phosphorus and sodium.

As regards feed compositions for ruminants such as cows, as well as ingredients thereof, the ruminant diet is usually composed of an easily degradable fraction (named concentrate) and a fiber-rich less readily degradable fraction (named hay, forage, or roughage).

Hay is made of dried grass, legume or whole cereals. Grasses include among others timothy, ryegrasses, fescues. Legumes include among others clover, lucerne or alfalfa, peas, beans and vetches. Whole cereals include among others barley, maize (corn), oat, sorghum. Other forage crops include sugarcane, kales, rapes, and cabbages. Also root crops such as turnips, swedes, mangles, fodder beet, and sugar beet (including sugar beet pulp and beet molasses) are used to feed ruminants. Still further crops are tubers such as potatoes, cassava and sweet potato. Silage is an ensiled version of the fiber-rich fraction (e.g. from grasses, legumes or whole cereals) whereby material with a high water content is treated with a controlled anaerobic fermentation process (naturally-fermented or additive treated).

Concentrate is largely made up of cereals (such as barley including brewers grain and distillers grain, maize, wheat, sorghum), but also often contain protein-rich feed ingredients such as soybean, rapeseed, palm kernel, cotton seed and sunflower.

Cows may also be fed total mixed rations (TMR), where all the dietary components, e.g. forage, silage and concentrate, are mixed before serving.

As mentioned above a premix is an example of a feed additive which may comprise the active compounds according to the invention. It is understood that the compounds may be administered to the animal in different other forms. For example the compounds can also be included in a bolus that would be placed in the rumen and that would release a defined amount of the active compounds continuously in well defined dosages over a specific period of time.

The present invention further relates to a method for reducing the production of methane emanating from the digestive activities of ruminants and/or for improving ruminant animal performance, comprising orally administering a sufficient amount of at least one organic molecule substituted at any position with at least one nitrooxy group, or a salt thereof as defined by formula (I) with the preferred embodiments described above.

Moreover, the invention further relates to a method as described above, wherein the compound of formula (I) is administered to the animal in combination with at least one additional active substance selected from the group consisting of: diallyl disulfide, garlic oil, allyl isothiocyanate, deoxycholic acid, chenodeoxycholic acid and derivatives thereof.

The invention also relates to a method as described above, wherein the ruminant animal is selected from the group consisting of: cattle, goats, sheep, giraffes, American Bison, European bison, yaks, water buffalo, deer, camels, alpacas, llamas, wildebeest, antelope, pronghorn, and nilgai, and more preferably from the group consisting of: cattle, goats and sheep.

The invention also relates to a method as described above, wherein the amount of the at least one active compound as defined in formula (I) administered to the ruminant animal is from about 1 mg to about 10 g per kg feed, preferably from about 10 mg to about 1 g, more preferably from 50 mg to 500 mg compound per kg of feed.

The invention also relates to a method as described above, wherein the methane production in ruminants calculated in liters per kilogram of dry matter intake is reduced by at least 10% when measured in metabolic chambers. Preferably, methane reduction is at least 15%, more preferably, at least 20%, even more preferably, at least 25%, most preferably, at least 30%. Alternative methane emission measurements may also be used like using a laser beam or for dairy ruminants, correlating methane production to the VFA profile in milk.

The invention also relates to a method as described above, wherein the ruminant feed conversion ratio is reduced by at least 1% when measured in conventional performance trial. Preferably, the feed conversion ratio is reduced by at least 2%, more preferably, by at least 2.5%, even more preferably, by at least 3%, most preferably, by at least 3.5%.

The present invention is further described by the following examples which should not be construed as limiting the scope of the invention.

EXAMPLES

Example 1

In Vitro Test for Methane Production

A modified version of the "Hohenheim Forage value Test (HFT)" was used for testing the effect of specific compounds on the rumen functions mimicked by this in-vitro system.
Principle:
Feed is given into a syringe with a composition of rumen liquor and an appropriate mixture of buffers. The solution is incubated at 39° C. After 8 hours the quantity (and composition) of methane produced is measured and put into a formula for conversion.

Reagents:
Mass Element Solution:
  6.2 g potassium dihydrogen phosphate ($KH_2PO_4$)
  0.6 g magnesium sulfate heptahydrate ($MgSO_4*7H_2O$)
  9 ml concentrated phosphoric acid (1 mol/l)
  dissolved in distilled water to 1 l (pH about 1.6)
Buffer Solution:
  35.0 g sodium hydrogen carbonate ($NaHCO_3$)
  4.0 g ammonium hydrogen carbonate ($(NH_4)HCO_3$)
  dissolved in distilled water to 1 l
Trace Element Solution:
  13.2 g calcium chloride dihydrate ($CaCl_2*2H_2O$)
  10.0 g manganese(II) chloride tetrahydrate ($MnCl_2*4H_2O$)
  1.0 g cobalt(II) chloride hexahydrate ($CoCl_2*6H_2O$)
  8.0 g iron(III) chloride ($FeCl_3*6H_2O$)
  dissolved in distilled water to 100 ml
Sodium Salt Solution:
  100 mg sodium salt
  dissolved in distilled water to 100 ml
Reduction Solution:
  first 3 ml sodium hydroxide (c=1 mol/l), then 427.5 mg sodium sulfide hydrate ($Na_2S*H_2O$) are added to 71.25 ml $H_2O$
  solution must be prepared shortly before it is added to the medium solution
Procedure:
Sample Weighing:
  The feed stuff is sieved to 1 mm—usually TMR (44% concentrate, 6% hay, 37% maize silage and 13% grass silage)—and weighed exactly into 64 syringes. 4 of these syringes are the substrate controls, which display the gas production without the effect of the tested compounds. 4 other syringes are positive control, in which bromoethane sulfonate has been added to 0.1 mM. When needed, 4 syringes contain a carrier control (if the test compounds need a carrier). The remaining syringes contain the test substances, by groups of 4 syringes.
Preparation of the Medium Solution:
  The components are mixed in a Woulff bottle in following order:
  711 ml water
  0.18 ml trace element solution
  355.5 ml buffer solution
  355.5 ml mass element solution
  The completed solution is warmed up to 39° C. followed by the addition of 1.83 ml sodium salt solution and the addition of reduction solution at 36° C. The rumen liquor is added, when the indicator turns colourless.
Extraction of the Rumen Liquor:
  750 ml of rumen liquor are added to approximately 1,400 ml of medium solution under continued agitation and $CO_2$-gassing.
Filling the Syringes, Incubation and Determining Gas Volumes and VFA Values:
  The diluted rumen fluid (24 ml) is added to the glass syringe. The syringes are then incubated for 8 hours at 39° C. under gentle agitation. After 8 hours, the volume of gas produced is measured, and the percentage of methane in the gas phase is determined by gas chromatography.
Results
  The food fermented was artificial TMR (44% concentrate, 6% hay, 37% maize silage and 13% grass silage). The compounds produced as described in examples 2 to 14 were added to the fermentation syringes to a concentration of 2 to 0.005 of dry matter (DM). The results are presented in the following table.

TABLE 3

Methane reduction effect resulting from the average of two experiments with some compounds according to the present invention (an integer in the column effect on methanogenesis change (%) means a reduction in methane produced when compared to control; no value means that the concentration was not tested)

| Structure | effect on methanogenesis (%) | | | | | | | |
|---|---|---|---|---|---|---|---|---|
| | 2% DM | 1% DM | 0.5% DM | 0.25% DM | 0.1% DM | 0.05% DM | 0.01% DM | 0.005% DM |
| HO~~~ONO$_2$ | 100 | | 100 | | 100 | 100 | 79 | 20 |
| PhCH$_2$CH$_2$CH(ONO$_2$)CH$_2$ONO$_2$ | 10 | | 4 | | | | | |
| (HOCH$_2$)$_3$C-CH$_2$ONO$_2$ | 85 | | 6 | | | | | |
| EtNHSO$_2$CH$_2$CH$_2$CH$_2$ONO$_2$ | 99 | | 99 | | 24 | 10 | | |
| O$_2$NO~~~~CN | | | | | 99 | 95 | 12 | 7 |
| NO$_2$O~~~~~ (pentyl nitrate) | | | | | 100 | 100 | 33 | 4 |
| EtC(O)O~~~ONO$_2$ | | | | | 100 | 100 | 21 | 6 |
| O$_2$NO~~~ONO$_2$ | | | | | 99 | 100 | 98 | 29 |
| O$_2$NO~~~~ONO$_2$ | | | | | 100 | 100 | 92 | 16 |
| O$_2$NO~~~~~ONO$_2$ | | | | | 100 | 100 | 45 | 6 |
| PhC(O)O~~~ONO$_2$ | | | 99 | | 99 | | 11 | |
| n-C$_5$H$_{11}$C(O)O~~~ONO$_2$ | | | 98 | | 99 | | 42 | |
| NO$_2$O~~~~C(O)O~~~ONO$_2$ | | | | | | | | |
| PhCH$_2$O-NO$_2$ | 100 | | 100 | | 37 | 3 | | |

TABLE 3-continued

Methane reduction effect resulting from the average of two experiments with some compounds according to the present invention (an integer in the column effect on methanogenesis change (%) means a reduction in methane produced when compared to control; no value means that the concentration was not tested)

| Structure | effect on methanogenesis (%) | | | | | | | |
|---|---|---|---|---|---|---|---|---|
| | 2% DM | 1% DM | 0.5% DM | 0.25% DM | 0.1% DM | 0.05% DM | 0.01% DM | 0.005% DM |
| [isosorbide dinitrate structure] | 100 | | | | | | | |
| [nicotinamide nitrooxy ethyl structure] | 100 | | | | | | | |
| [diethylene glycol dinitrate structure] | | | | | 100 | 99 | 64 | 3 |

Example 2

Comparative Example: In Vitro Test for Methane Production

The same in vitro assay as described in example 1 has been performed with a series of molecules, wherein the nitrooxy group has been replaced by different organic groups. Moreover, the inorganic salt Na NO3 has also been tested. See results in Table 4. This data demonstrates that a significant methane reduction activity is only observed when the Nitrooxy group is present in the series.

TABLE 4

Methane reduction effect resulting from the average of two experiments with 3-nitrooxypropanol according to the present inventionin comparison with similar compounds in which the nitrooxy group has been replaced. (An integer in the column effect on methanogenesis change (%) means a reduction in methane produced when compared to control; no value means that the concentration was not tested)

| Structure | effect on methanogenesis (%) | | | | |
|---|---|---|---|---|---|
| | 2% DM | 0.5% DM | 0.1% DM | 0.05% DM | 0.01% DM |
| HO~~~ONO2 | 100 | 100 | 100 | | 79 |
| HO~~~NO2 | | | | | 2 |
| HO~~~O~ | | | | | 8 |
| HO~~~C(O)O-ethyl | | | | | 6 |

TABLE 4-continued

Methane reduction effect resulting from the average of two experiments with 3-nitrooxypropanol according to the present inventionin comparison with similar compounds in which the nitrooxy group has been replaced. (An integer in the column effect on methanogenesis change (%) means a reduction in methane produced when compared to control; no value means that the concentration was not tested)

| Structure | effect on methanogenesis (%) | | | | |
|---|---|---|---|---|---|
| | 2% DM | 0.5% DM | 0.1% DM | 0.05% DM | 0.01% DM |
| HO~~~NH2 | | | | | 2 |
| Na NO3 | 23 | 2 | | | |

Example 3

Synthesis of 3-Nitrooxypropanol

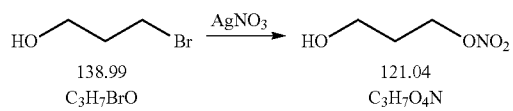

138.99  121.04
C$_3$H$_7$BrO  C$_3$H$_7$O$_4$N 50.1 mmol 3-Bromopropanol dissolved in 100 ml acetonitrile and 125.25 mmol silver nitrite were added into a flask protected from light. This suspension was stirred for 21 hours at 70° C. After cooling to room temperature the suspension was filtrated and concentrated in vacuo. The residue was dissolved in Water and extracted two times with TMBE. The organic phases were washed with water and brine, combined, dried over Na$_2$SO$_4$ and the solvent was removed in vacuo leaving 5.63 g.

The crude product was purified by flash chromatography on silica gel using heptane/ethyl acetate 2:1; Yield: 4.82 g (38.8 mmol, 77.4%).

Example 4

Synthesis of 2-(Hydroxymethyl)-2-(nitrooxymethyl)-1,3-propanediol

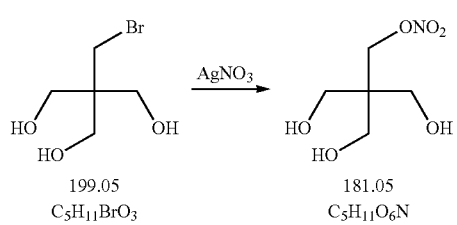

199.05
C$_5$H$_{11}$BrO$_3$ 181.05
C$_5$H$_{11}$O$_6$N 5 mmol 2-(Bromomethyl)-2-(hydroxymethyl)-1,3-propanediol dissolved in 20 ml acetonitrile and 15 mmol silver nitrite were added into a flask protected from light. This suspension was stirred for 24 hours at 70° C. After cooling to room temperature the suspension was filtrated and the solvent was removed in vacuo leaving 3.05 g.

The crude product was purified by flash chromatography on silica gel using dichloromethane/methanol 50:1; Yield: 0.36 g (1.99 mmol, 40.2%).

Example 5

Synthesis of rac-4-Phenylbutane-1,2-diyldinitrate

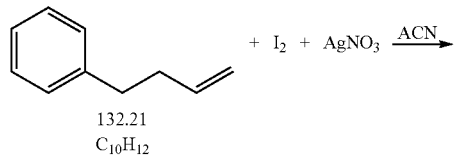

132.21
C$_{10}$H$_{12}$ 256.22
C$_{10}$H$_{12}$N$_2$O$_6$ 7.5 mmol 4-Phenyl-1-buten dissolved in 40 ml acetonitrile, 20.3 mmol silver nitrite and 7.5 mmol Iode were added into a flask protected from light. This suspension was stirred for 30 minutes at 25° C. and then for 16 hours at 79° C. After cooling to room temperature the suspension was filtrated and washed with Ethyl acetate. The filtrate was extracted three times with water and washed brine, dried over Na$_2$SO$_4$ and the solvent was removed in vacuo leaving 1.92 g.

The crude product was purified by flash chromatography on silica gel using Hexane/Ethyl acetate 10:1; Yield: 0.52 g (2.03 mmol, 27%).

Example 6

Synthesis of N-Ethyl-3-nitrooxy-propionic sulfonyl amide

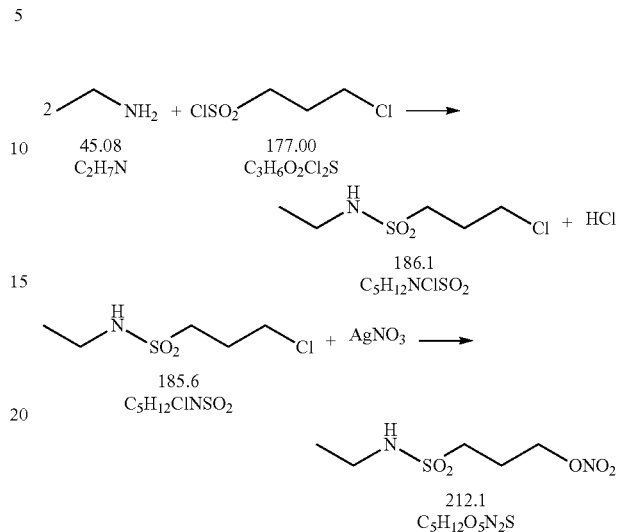

45.08
C$_2$H$_7$N 177.00
C$_3$H$_6$O$_2$Cl$_2$S 186.1
C$_5$H$_{12}$NClSO$_2$ 185.6
C$_5$H$_{12}$ClNSO$_2$ 212.1
C$_5$H$_{12}$O$_5$N$_2$S

In a flask 17 mmol 3-chloropropionic sulfonyl chloride were dissolved in 5 ml Tetrahydrofurane. 33.3 mmol Ethylamine were added over a period of 45 minutes. After that, the solvent was removed in vacuo. The residue was dissolved in water, extracted three times with ethyl acetate. The combined organic phases were washed with brine, dried over Na$_2$SO$_4$ and the solvent was removed in vacuo.

The residue was dissolved in 50 ml acetonitrile and 60 mmol silver nitrite were added into a flask protected from light. This suspension was stirred for 41 hours at 70° C. After cooling to room temperature the suspension was filtrated and concentrated in vacuo. The residue was dissolved in dichloromethane and extracted with Water. The water phase was washed again with two times with dichloromethane. The combined organic phase was washed with water and brine, dried over Na$_2$SO$_4$ and the solvent was removed in vacuo; Yield: 3.05 g (14.5 mmol; 84.5%).

Example 7

Synthesis of 3-Nitrooxy-propyl propionate

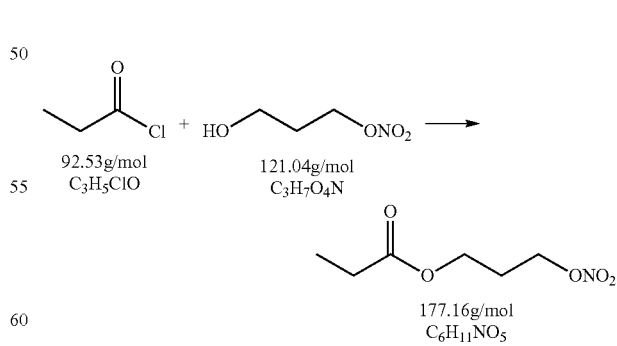

92.53g/mol
C$_3$H$_5$ClO 121.04g/mol
C$_3$H$_7$O$_4$N 177.16g/mol
C$_6$H$_{11}$NO$_5$ 9.1 mmol Propionyl chloride were dissolved in 10 ml TMBE and cooled to 3° C. 8.25 mmol 3-Nitrooxypropanol and 9.1 mmol triethylamine in 5 ml TMBE were dropped over a period of 5 min at 3 to 6° C. After 2 hours and 30 minutes stirring without cooling the reaction mixture were extracted with 1N HCl, twice with water, washed with brine, dried over $Na_2SO_4$ and the solvent was removed in vacuo leaving 1.35 g.

The crude product was purified by flash chromatography on silica gel using Hexane/Ethyl acetate 4:1; Yield: 1.14 g (6.4 mmol, 78.0%).

Example 8

Synthesis of 3-Nitrooxy-propyl benzoate

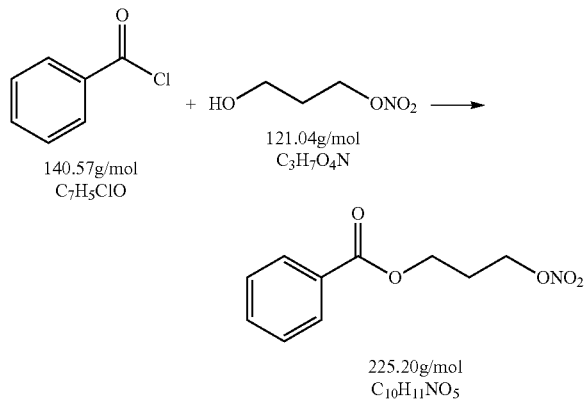

16.5 mmol 3-Nitrooxypropanol dissolved in 10 ml TMBE and 18.2 mmol Triethylamine were cooled to 3° C. 18.2 mmol benzoylchloride in 5 ml TMBE were dropped over a period of 7 minutes at 3 to 6° C. After 24 hours and 30 minutes stirring without cooling, the reaction mixture was extracted with sated. $NaHCO_3$, water, 1N HCl, twice with water, washed with brine, dried over $Na_2SO_4$ and the solvent was removed in vacuo leaving 3.3 g.

The crude product was purified by flash chromatography on silica gel using a gradient of Hexane/Ethyl acetate from 1:0 to 2:1; Yield: 0.66 g (2.9 mmol, 17.7%).

Example 9

Synthesis of 3-Nitrooxy-propyl hexanoate

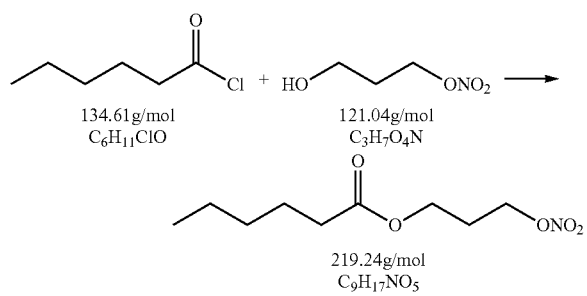

20 mmol 3-Nitrooxypropanol dissolved in 10 ml Diethylether and 20 mmol Triethylamine were cooled to 0° C. 18.2 mmol hexoylchlorid were dropped over a period of 5 minutes at 0 to 5° C. After 19 hours stirring without cooling, the reaction mixture was extracted with 1N HCl, twice with water, washed with brine, dried over $Na_2SO_4$ and the solvent was removed in vacuo leaving 3.1 g.

The crude product was purified by flash chromatography on silica gel using Heptane/Ethyl acetate 4:1; Yield: 2.4 g (10.9 mmol, 60.0%).

Example 10

Synthesis of 3-Nitrooxy-propyl 5-nitrooxy-hexanoate

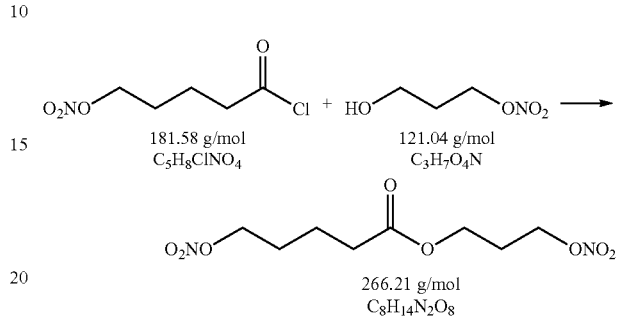

20 mmol 3-Nitrooxypropanol dissolved in 10 ml Diethylether and 20 mmol Triethylamine were cooled to 0° C. 18.2 mmol 5-nitrooxypentoylchlorid were dropped over a period of 5 min at 0 to 5° C. After stirring over night without cooling, the reaction mixture was extracted with 1N HCl, twice with water, washed with brine, dried over $Na_2SO_4$ and the solvent was removed in vacuo.

The crude product was purified by flash chromatography on silica gel using Heptane/Ethyl acetate 4:1; Yield: 2.4 g (9.1 mmol, 50.0%).

Example 11

Synthesis of Benzylnitrate

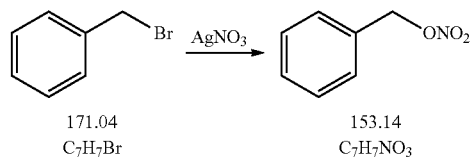

10 mmol Benzylbromide dissolved in 80 ml acetonitrile and 25 mmol silver nitrite were added into a flask protected from light. This suspension was stirred for 5 hours at 70° C. After cooling to room temperature the suspension was filtrated and concentrated in vacuo. The residue was dissolved in dichloromethane and extracted with Water. The water phase was washed again with two times with dichloromethane. The combined organic phase was washed with water and brine, dried over $Na_2SO_4$ and the solvent was removed in vacuo; Yield: 1.55 g (10.1 mmol; 100%).

Example 12

Synthesis of 1,3-bis-Nitrooxy-propane

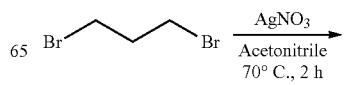

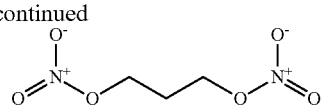

To a solution of 1,3-dibromopropane (2.00 g, 1.0 eq) in 20.0 mL of dry acetonitrile was added Silver Nitrate (3.70 g, 2.2 eq). The reaction mixture was heated at 70° C. for 2 hours in the dark. The resulting mixture was filtered off through celite and the filtrate was concentrated. The residue was dissolved into water (50.0 mL), extracted with dichloromethane (2×50.0 mL), dried over magnesium sulfate and solvents were evaporated under vacuum to afford 1.44 g of compound as a colorless liquid (Yield=87%).

Example 13

Synthesis of 1,4-bis-Nitrooxy-butane

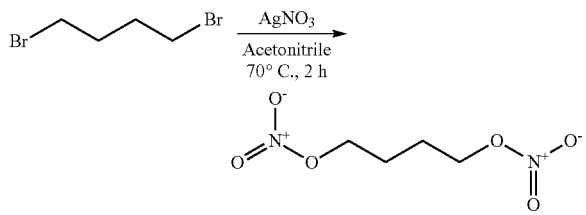

To a solution of 1,4-dibromobutane (2.00 g, 1.0 eq) in 20.0 mL of dry acetonitrile was added Silver Nitrate (3.50 g, 2.2 eq). The reaction mixture was heated at 70° C. for 2 hours in the dark. The resulting mixture was filtered off through celite and the filtrate was concentrated. The residue was dissolved into water (50.0 mL), extracted with dichloromethane (2×50.0 mL) and dried over magnesium sulphate. Solvents were evaporated under vacuum to afford 1.49 g of compound as a colorless liquid (Yield=89%).

Example 14

Synthesis of 1,5-bis-Nitrooxy-pentane

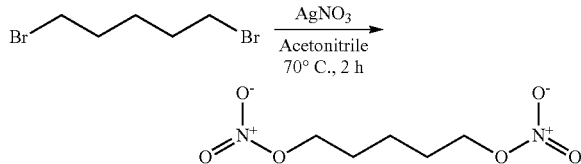

To a solution of 1,5-dibromopentane (2.00 g, 1.0 eq) in 20.0 mL of dry acetonitrile was added Silver Nitrate (3.30 g, 2.2 eq). The reaction mixture was heated at 70° C. for 2 hours in the dark. The resulting mixture was filtered off through celite and the filtrate was concentrated. The residue was dissolved into water (50.0 mL), extracted with dichloromethane (2×50.0 mL) and dried over magnesium sulphate. Solvents were evaporated under vacuum to afford 1.38 g of compound as a colorless liquid (Yield=82%).

Example 15

Synthesis of 5-Nitrooxy-pentanenitrile

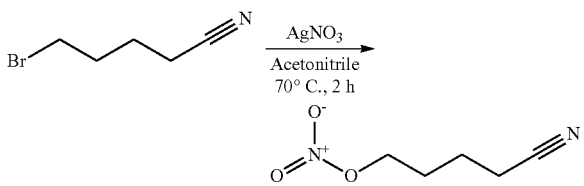

To a solution of 5-bromovaleronitrile (4.00 g, 1.0 eq) in 40.0 mL of dry acetonitrile was added Silver Nitrate (4.60 g, 1.1 eq). The reaction mixture was heated at 70° C. for 2 hours in the dark. The resulting mixture was filtered off through celite and the filtrate was concentrated. The residue was dissolved into water (50.0 mL), extracted with dichloromethane (2×50.0 mL) and dried over magnesium sulphate. Solvents were evaporated under vacuum to afford 3.56 g of compound as a colorless liquid (Yield=99%).

Example 16

In Vivo Effect of 3-Nitrooxypropanol Compared to ethyl-3-nitrooxypropionate

Material and Methods 10 sheep were cannulated in the rumen. The trial started one month after the surgical operation. There were 3 treatments: control, additive 1 and additive 2, both at a single dose. Additive 1 is ethyl-3-nitrooxypropionate, and additive 2 is 3-nitrooxypropanol of the present invention. The experimental design consisted of a 3×3 Latin square with 3 sheep per treatment in each period and 3 consecutive periods. Each period included 28 days of adaptation to the treatment plus two consecutive days of methane measurements in chambers and collection of rumen samples. Over the course of the adaptation phase, a medium term one day methane measurement was done at day 14. In addition, during days 22 and 23 samples of alfalfa hay and oats, placed in nylon bags, were incubated in the rumen of sheep to determine the dry matter ruminal degradation. During the two days of methane measurements in chambers (days 29 and 30) rumen contents samples were collected two hours after the morning feeding, sub-sampled and immediately frozen prior DNA extraction and determination of volatile fatty acids and ammonia nitrogen concentration. Experimental animals were randomly allocated in three sub-groups of 3 animals each and were randomly assigned one of the three treatments (control, additive 1 and additive 2). The 3 sub-groups started the adaptation to the diet with a gap of two days so they were in the same adaptation day prior methane measurement in the chambers. Animals were individually held in cages with constant access to fresh water. A diet consisting of alfalfa hay chopped at 15-20 cm and oats in a 60:40 ratio plus mineral-vitamin supplement was provided to the animals at approximately 1.1 times the energy maintenance level in two equal meals at 9'00 and 14'00 hours. Fresh matter intake was monitored daily for each animal throughout the trial.

The additive was provided twice a day through the ruminal cannula at the same time as the feed. The corresponding amount to each additive (100 mg per animal and day for both additives) was pipetted into 10 grams of grounded oats and wrapped in cellulose paper immediately before it was placed in the rumen. Since the active molecule is volatile the previously mentioned procedure was carried out in a cold room at 4° C.

Methane Measurement and Samples Collection

A set of four methane chambers was used. On days 14, 29 and 30 animals were placed in the chambers for methane measurements. Each chamber measured 1.8 m wide×1.8 m deep×1.5 m tall. Chamber air temperature was maintained between 15 and 20° C. Within each chamber, the animals were individually restrained in the same cages as during adaptation. Interruptions occurred daily at 09'00 hours, when the chamber floor was cleaned, and the animals were fed. These interruptions had little impact on the daily methane emissions because fluxes were calculated three times per day and then averaged to derive the 23-h emission value.

Airflow and concentration of methane was measured for the inflow and outflow ducts of each chamber. Air velocity was continuously monitored over the day in the exhaust duct for each chamber. The air stream in each of the 4 ducts (chambers 1, 2 and 3 and background) was sub-sampled, and methane concentration was measured continuously using a gas analyzer ADM MGA3000 (Spurling works, Herts, UK). It took 11 min to sequentially sample the airflow in all inflow and exhausts ducts in the chambers (3 min in chambers 1, 2, 3, 2 min for background). In summary, the flux of methane for each chamber was calculated for each measuring day from the difference of fresh-air inflow and chamber exhaust methane concentrations and mean air velocities.

Rumen Samples Analysis

Samples of rumen contents were freeze-dried and thoroughly mixed by physical disruption using a bead beater (Mini-bead Beater; BioSpec Products, Bartlesville, Okla., USA) before DNA extraction, which was performed from approximately 50 mg of sample using the QIAamp® DNA Stool Mini Kit (Qiagen Ltd, West Sussex, UK) following the manufacturer's instructions with the modification that a higher temperature (95° C.) was used for lysis incubation. DNA samples were used as templates for quantitative real-time PCR (qPCR) amplification. The abundance of total bacteria, total protozoa and total methanogenic archaea were quantified by Real Time—PCR (qPCR). Different primer sets were used to amplify 16S rRNA gene-targeted total bacteria (Maeda et al., 2003), and 18S rRNA gene-targeted total protozoa (Sylvester et al 2005). Primers designed for the detection of methanogenic archaea were targeted against the methyl coenzyme-M reductase (mcrA) gene (Denman et al., 2007). The amplifications mixture contained 11.5 µl 2×RT-PCR supermix BioRad (Bio-Rad Laboratories Inc., Hercules, Calif., USA), 0.4 µl of each primer and 0.5 µl of sample in a final volume of 23 µl. The amplification efficiency was evaluated for each pair of primers with the following program: a 5 min cycle at 95° C., 40 cycles at 95° C. for 15 s, 60° C. for 30 s, 72° C. for 55 s and, 75° C. during 6 s for fluorescent emission measures. The melting curve was built by increasing temperature from 55° C. to 95° C. and readings were taken every 5° C. Amplification of each target group was carried out with the following program: a 5 min cycle at 95° C., 40 cycles at 95° C. for 15 s, 15 s at 60° C. and 72° C. for 45 s (including the fluorescence emission measuring) and a melting curve with a set point temperature of 45° C. and end temperature of 95° C. The absolute amount of bacteria, protozoa and methanogenic archaea, expressed as the number of DNA copies, was determined by using the plasmid pCR®4-TOPO (Invitrogen™, Carlsbad, Calif., USA) as standard. The PCR product obtained using the respective set of primers was purified and then cloned into pCR® 4-TOPO® plasmid (Invitrogen™, Carlsbad, Calif., USA) to produce recombinant plasmids. A single colony, verified for the expected insert using PCR, was grown in solid media with antibiotics and X-gal overnight. Afterwards, a screening of transformed E. coli colonies was done and some of the positive ones were randomly selected. After checking the presence of the inserted fragment in the colonies by PCR, massive culture of positive colonies was done in liquid media overnight. Plasmids belonging to these cultures were extracted using the Pure Link™ Miniprep kit (Invitrogen™, Carlsbad, Calif., USA) and then sequenced to verify the presence of the fragment inserted. The number of 16S rRNA gene copies present in the plasmid extracts was calculated using the plasmid DNA concentration and the molecular mass of the vector with the insert. The concentrated plasmid was serially diluted (10-fold) to provide a range of $10^8$ to $10^2$ copies to generate a standard curve.

A relative abundance quantification was used for methanogenic archaea and protozoa as described by Denman and McSweeny (2006) using the 16sRNA as reference gene. Volatile fatty acids were analysed by gas chromatography and ammonia N concentration by colorimetry following the protocols established in our laboratory (Martin-Garcia et al., 2004).

Rumen Degradability

Three grams of 2 mm ground feed were placed in 5 cm×10 cm nylon bags with a pore size of 50 µm (#R510 Ankom in situ bags, Macedon N.Y.). The two ingredients used in the animals' diets were tested: oats and alfalfa hay. Bags with oats were incubated in the rumen for 24 hours, while those with alfalfa hay for 48 hours. The incubations times were chosen based on average residing times in the rumen of different feedstuffs. On days 22 and 23 two bags per feed and animal and period were. Bags were placed in the rumen immediately before the morning feeding. At 24 or 48 hours they were taken out of the rumen, washed with cold water and frozen at −20° C. At the end of every period the frozen bags were washed in a washing machine using a short cold water program including two bags per feed that had not been incubated in the rumen to account for solubility. After washing, the bags were placed in the oven at 60° C. for 48 hours. Rumen degradability (%) was calculated as the loss of dry matter over the incubation time.

Experimental Animals Care

All management and experimental procedures to the sheep were carried out by trained personnel in strict accordance with the Spanish guidelines (Act No. 1201/2005 of 10 Oct. 2005) for experimental animal protection. The temperature, humidity and air turn out in chambers were carefully monitored considering the animal welfare conditions. $CO_2$ concentration was also continuously monitored in order to keep it within the limits that ensured a good air quality and renovation rate. Animals didn't show any stressed behaviour while they were allocated in chambers.

Statistical Analysis

Individual methane emissions, VFA profiles, ratio of acetate to propionate, ammonia N concentration, $\log_{10}$ transformations of concentration of total bacteria, total protozoa and methanogenic archaea and the relative abundance were analyzed for effect of including the additive. The standard error of the mean (SEM) was computed for each analysis. Means were further compared using a least significant difference (LSD) test.

Results

Dry matter intake was not affected (P>0.05) by the treatment and only slight reduction in intakes were observed when the animals were introduced in the methane chambers on days 14 and 30.

As described for intakes, the body weight (as an average of weights recorded prior and after chamber measurements) was not different (P>0.05) among treatments (Table 5). Methane emissions, expressed as liters per kg of fresh matter intake, were significantly (P=0.020) reduced on day 14 when both additives were incorporated in the diet. The reduction observed against the control was 14% and 23%, respectively, for additives 1 and 2. When methane emissions were recorded two weeks later, on days 29 and 30, there was still a numerically reduction, although it did not reach the statistical significance (P=0.061 and 0.183 for days 29 and 30, respectively). If the measurements recorded during the last two consecutive days are pooled together the effect of the addition shows a similar tendency (P=0.092) as the values considered separately.

TABLE 5

Effect of the addition of additives 1 and 2 on body weights, intakes and methane emissions by sheep measured on days 14, 29 and 30 after commencing the treatment.

| Time | Item | Control | Additive 1 | Additive 2 | SEM | P value |
|---|---|---|---|---|---|---|
| day 14 | intake, kg/day | 0.819 | 0.849 | 0.867 | | |
| | CH4 l, day | 24.6 | 21.9 | 20.0 | | |
| | CH4 l/kg intake | 29.9 | 25.6 | 22.5 | 2.31 | 0.020 |
| day 29 | intake, kg/day | 0.856 | 0.944 | 0.922 | | |
| | CH4 l, day | 22.0 | 20.9 | 18.3 | | |
| | CH4 l/kg intake | 25.8 | 21.7 | 19.6 | 2.12 | 0.061 |
| day 30 | intake, kg/day | 0.760 | 0.925 | 0.747 | | |
| | CH4 l, day | 22.7 | 21.8 | 19.7 | | |
| | CH4 l/kg intake | 29.8 | 23.2 | 25.6 | 2.34 | 0.183 |
| days 29-30 | intake, kg/day | 0.780 | 0.933 | 0.823 | | |
| | CH4 l, day | 21.8 | 21.5 | 19.1 | | |
| | CH4 l/kg intake | 28.2 | 22.6 | 23.1 | 2.17 | 0.092 |

$^{a,b}$Values in a row not sharing a common superscript letters significantly differ, P < 0.05.
*Average of weighing prior and after chamber measurements.
SEM: Standard Error of the Means

TABLE 6

Effect of the addition of additive 1 and 2 on volatile fatty acid profile (mol/100 mol), ammonia N concentration (mg/100 ml) and dry matter degradation (DMD, %) of oats (24 hours) and alfalfa hay (48 hours) in the rumen of sheep.

| | Control | Additive 1 | Additive 2 | SEM | P value |
|---|---|---|---|---|---|
| Acetate | 69.2$^c$ | 67.5$^b$ | 64.5$^a$ | 0.742 | 0.007 |
| Propionate | 14.3$^a$ | 16.6$^a$ | 17.5$^b$ | 1.030 | 0.004 |
| Butirate | 2.08 | 2.05 | 2.11 | 0.818 | 0.353 |
| iso-butirate | 11.2 | 10.1 | 12.3 | 0.201 | 0.995 |
| Valerate | 1.91 | 1.94 | 1.82 | 0.194 | 0.100 |
| iso-valerate | 1.47 | 1.79 | 1.82 | 0.281 | 0.908 |
| Total | 57.4 | 58.2 | 57.1 | 5.193 | 0.995 |
| C2/C3 | 4.91$^b$ | 4.09$^a$ | 3.89$^a$ | 0.262 | 0.002 |
| N—NH$_3$ | 100.1 | 97.3 | 104.1 | 9.157 | 0.924 |
| DMD alfalfa hay | 78.6 | 78.3 | 78.8 | 1.22 | 0.725 |
| DMD oats | 74.2 | 74.0 | 70.6 | 2.02 | 0.167 |

$^{a,b}$Values in a row not sharing a common superscript letters significantly differ, P < 005.
SEM: Standard Error of the Means The study of the rumen fermentation parameters from rumen samples collected on days 29 and 30 showed a shift in the fermentation pathways (Table 5) towards a more propionate type profile in the rumen of animals receiving both additives in comparison to the control. As a consequence, in both treatments the acetate to propionate ratio was significantly (P=0.002) reduced. The concentration of ammonia N was similar among treatments and within the range expected for the diet supplied to the animals.

The in sacco degradation study on days $22^{nd}$ and $23^{rd}$ showed no effect of the additive treatment on the rumen degradability of both alfalfa hay and oats.

TABLE 7

Effect of the addition of additives 1 and 2 on the concentration (log copy gene numbers/g fresh matter) of total bacteria (16S rRNA), protozoa (18S rRNA) and methanogenic archaea (mcrΔ gene) in the rumen of sheep. The relative abundance (ΔCt) in relation to total bacteria is also shown for protozoa and methanogens.

| | Control | Additive 1 | Additive 2 | Error | P value |
|---|---|---|---|---|---|
| Total bacteria | 7.45 * 10$^{10}$ | 9.08 * 10$^{10}$ | 9.74 * 10$^{10}$ | | |
| log10 | 10.8 | 10.9 | 11.0 | 0.123 | 0.607 |
| Total protozoa | 2.84 * 10$^{10}$ | 1.87 * 10$^{10}$ | 2.51 * 10$^{10}$ | | |
| log 10 | 10.4 | 10.2 | 10.2 | 0.212 | 0.702 |
| ΔCt | 1.65 | 1.58 | 1.55 | 0.267 | 0.984 |
| Archaea | 3.54 * 10$^8$ | 2.86 * 10$^8$ | 2.86 * 10$^8$ | | |
| log10 | 8.54 | 8.45 | 8.34 | 0.133 | 0.511 |
| ΔCt | 0.028 | 0.022 | 0.020 | 0.005 | 0.602 |

Total and relative concentration of the analysed microbial groups in the rumen showed no difference (P>0.05) among treatments. When the abundance of both protozoa and methanogenic archaea were expressed relative to total bacteria the same lack of effect was observed.

Conclusions

The use of both additives resulted in a significant reduction of methane production and, according to the VFA profiles, a shift in the metabolic pathways involved in $H_2$ transferring was promoted by additives as well. The objective of this trial was to confirm whether the treatment of animals for a month showed a persistence of the results observed over two weeks treatment. This is essential when assessing the suitability of the practical use of a feed additive. In this study both additives showed effect over a month treatment in methane emissions that was further confirmed by a shift in the fermentation pattern.

On the other hand, a change in the fermentation pattern might be not only due to a reduction in methane production but also to a lower fibre degradation which, in turn, would produce less acetate and therefore lowered acetate to propionate ratio. In order to rule out this occurring, a rumen degradability assessment was carried out by incubating nylon bags with both oats and alfalfa hay in the rumen of the animals.

The results showed no such effect on dry matter degradation which is also supported by the same bacterial and protozoa biomass recorded in animals receiving the additives compared to those with no treatment.

Example 17

In Vivo Effect of 3-Nitrooxypropanol in Dairy Cows

Material and Methods

Animals: Six rumen fistulated lactating Holstein X Friesian dairy cows of second or greater parity and weighing from 550 to 800 kg were used for the study. Cows were in mid lactation at the start of the study.

Experimental diets: A single total mixed ration (TMR) diet was provided to all cows throughout the study. Cows were fed ad libitum (5% refusals) for the duration of the trial.

Experimental design: Beginning in mid lactation (with milk yields of 30 liters or more), the six cows were randomly assigned to one of the three supplement treatments in a 3×3 Latin Square design (Table 8). Treatment periods were 5 weeks in duration.

TABLE 8

Experimental design

| | Cow | | | | | |
|---|---|---|---|---|---|---|
| | Pair 1 | | | Pair 2 | Pair 3 | |
| | Square 1 | | | Square 2 | | |
| Period | Cow 888 | Cow 989 | Cow 973 | Cow 1000 | Cow 1030 | Cow 1060 |
| 1 | 1 | 2 | 3 | 1 | 2 | 3 |
| 2 | 2 | 3 | 1 | 2 | 3 | 1 |
| 3 | 3 | 1 | 2 | 3 | 1 | 2 |

Diets: 1—Control 2—3-Nitrooxypropanol (500 mg/day) 3—3-Nitrooxypropanol (2500 mg/day)

Dosing of 3-Nitrooxypropanol or placebo: The doses of 3-Nitrooxypropanol or placebo was administered to the animals via the rumen cannula at feeding time in the morning and evening.

Period Design: As only two cows can be housed in the indirect calorimeters at any one time cows were run in pairs staggered by one week. At the end of week 4 animals were moved to the indirect calorimeters and held in individual tie stalls where four complete 24 hr measurements of respiratory exchange (methane and carbon dioxide production and oxygen consumption) were obtained (Cammell et al., 2000).

Results

Feed Intake: There was no significant effect of the product (3-Nitrooxypropanol) on daily dry matter intake (DMI) (see table 9).

Methane Production: Methane production (liters/d) and methane yield (liters/kg DMI) were significantly reduced by the 3-Nitrooxypropanol. Methane production was 93 and 90% of control values when the 500 and 2500 mg/d doses were given, respectively (see table 9). As regards methane yield, the corresponding values were 96 and 93% of control methane yield, respectively, for the low and high doses.

TABLE 9

Effects of DSM product fed at two doses.

| | Daily dose, mg/d | | | |
|---|---|---|---|---|
| | 0 | 500 | 2500 | SEM |
| DMI, kg/d | 18.9 | 18.8 | 18.5 | 0.7 |
| $CH_4$, L/d | 594 | 555 | 536 | 15.3 |
| $CH_4$, g/d | 425 | 398 | 384 | 11.0 |
| $CH_4$, L/kg DMI | 31.3 | 29.9 | 29.2 | 1.2 |

Large variations were observed between animals some showing more response that some others. These results show the potential of the compounds of the present invention in reducing methane production in dairy cows, and shed light on further improving the feeding regimen.

The invention claimed is:

1. A feed composition or feed additive for a ruminant comprising an amount between about 1 mg to about 10 g/kg of feed of 3-nitrooxy propanol sufficient to reduce production of methane emanating from digestive activities of a ruminant by at least 10% calculated in liters per kilogram of dry matter intake when measured in a metabolic chamber.

2. A feed composition or feed additive for reducing the production of methane emanating from the digestive activities of ruminants, wherein the feed composition comprises an amount between about 1 mg/kg of feed to about 10 g/kg of feed sufficient to reduce production of methane emanating from the digestive activities of a ruminant of at least one active organic molecule or a salt thereof selected from the group consisting of 3-nitrooxypropanol, rac-4-phenylbutane-1,2-diyldinitrate, 2-(hydroxymethyl)-2-(nitrooxymethyl)-1,3-propanediol, N-ethyl-3-nitrooxy-propionic sulfonyl amide, 5-nitrooxy-pentanenitrile, 5-nitrooxy-pentane, 3-nitrooxy-propyl propionate, 1,3-bis-nitrooxypropane, 1,4-bis-nitrooxybutane, 1,5-bis-nitrooxypentane, 3-nitrooxypropyl benzoate, 3-nitrooxy-propyl hexanoate, 3-nitrooxypropyl 5-nitrooxy-hexanoate, benzylnitrate, isosorbiddinitrate, N-[2-(nitrooxy)ethyl]-3-pyridinecarboxamide, and bis-(2-nitrooxyethyl) ether.

3. The feed composition or feed additive according to claim 2 which is a mineral premix, a vitamin premix, or a premix including vitamins and minerals or a bolus.

4. The feed composition or feed additive according to claim 2, wherein the at least one active organic molecule is 3-nitrooxy propanol.

5. The feed composition or feed additive according to claim 2, wherein the at least one active organic molecule is a mixture of 3-nitrooxy propanol and 1,3-bis-nitrooxypropane.

* * * * *